United States Patent [19]

Ashmead

[11] Patent Number: 4,599,152
[45] Date of Patent: Jul. 8, 1986

[54] PURE AMINO ACID CHELATES

[75] Inventor: Harvey H. Ashmead, Kaysville, Utah
[73] Assignee: Albion Laboratories, Clearfield, Utah
[21] Appl. No.: 738,065
[22] Filed: May 24, 1985
[51] Int. Cl.$^4$ ................................................. C25B 1/02
[52] U.S. Cl. ...................................... 204/72; 204/129; 260/113; 260/115
[58] Field of Search .......................... 204/129, 128, 72; 260/115, 113

[56] References Cited

U.S. PATENT DOCUMENTS 3,040,018 6/1962 Wingerd ............................ 260/115
4,495,176 1/1985 Brule et al. ........................ 260/115

Primary Examiner—R. L. Andrews
Attorney, Agent, or Firm—Thorpe, North and Western

[57] ABSTRACT

Pure amino acid chelates and a method of their production are disclosed. The amino acid chelates are free of contaminating inorganic anions. The chelate consists of a metal ion comprising iron, zinc, manganese, magnesium, copper, calcium and mixtures thereof. The metal ion is chelated to one or more ligands comprising alpha amino acids, protein hydrolysates, polypeptides, dipeptides, and combinations thereof. A novel process is disclosed wherein the amino acid ligand is brought into reactive contact with a divalent metal ion in an environment which is completely anion free but otherwise conducive to the interaction between the amino acid ligand and the metal ion, with the formation of an amino acid chelate in pure form or, at least, which can readily be recovered from the reactive environment in pure form.

8 Claims, No Drawings

PURE AMINO ACID CHELATES

BACKGROUND OF THE INVENTION

This invention relates to pure amino acid chelates and to a method of their preparation. More specifically, this invention relates to pure amino acid chelates which are free of contaminating anions and to a method of chelate preparation.

Amino acid chelates are becoming well accepted as a means of increasing the metal content in biological tissues of man, animals and plants. By amino acid chelates is meant the product resulting from the reaction of a polypeptide, dipeptide or naturally occuring alpha amino acid with a metal ion having a valence of two or more to form a ring structure wherein the positive electrical charges of the metal ion are neutralized by the electrons available through the carboxylate or free amino groups of the alpha amino acid. For convenience sake metal ions having a valence of two or more will simply be referred to as divalent metal ions or divalent cations. For the same reasons naturally occurring alpha amino acids will be referred to as amino acids. Although the term amino acid as used throughout this specification refers only to products obtainable through the hydrolysis of proteins, that does not mean that synthetically produced amino acids are to be excluded provided they are the same as can be obtained through the hydrolysis of proteins. Therefore, protein hydrolysates such as polypeptides, dipeptides and naturally occuring alpha amino acids are collectively referred to as amino acids. Now included within in this terminology are synthetically produced amino acids such as ethylenediaminetetraacetic acid (EDTA), monohydroxyethylethylenediaminetriacetic acid, diethylenetriaminepentaacetic acid, monohydroxyethyldiglycine and dihydroxyethylglycine, all of which are utilized as chelating agents for industrial purposes. These synthetic amino acids are outside the scope of this invention.

There are numerous reasons for limiting the scope of the invention to the amino acids defined. These amino acids are important building blocks for proteins and function as such when ingested into biological tissues. In addition, the chemistry is different between substituted and naturally occuring amino acids. EDTA type of ligands are strong chelating agents forming chelates having high stability constants of the order of $10^{16-28}$. EDTA type chelates may pass intact through most biological systems and not contribute to such systems by making a mineral more bioavailable or by adding protein building blocks. EDTA types of chelating agents are most often administered as metal scavengers to remove unwanted cations from biological systems. Amino acid chelates, on the other hand, are sufficiently stable that they are absorbed intact into biological systems where the chelate bonding is broken and the metal ion and amino acids are utilized by the system at the appropriate sites. In an animal, for example, most metal absorption occurs in the small intestine. The amino acid chelates have been found to have stability constants which are sufficent to hold the chelate intact while it is absorbed into biological tissues. Once absorbed, it is broken down by the system and the metal ion and amino acid ligand portion are then utilized as needed.

Chelate formation through neutralization of the positive charges of the divalent metal ions can be through the formation of ionic, covalent or coordinate covalent bonding. In the past, amino acid chelates have generally been made by first dissolving a water soluble divalent metal salt in water. An amino acid ligand is then reacted with the metal ion at a ratio of ligand to metal of at least 2:1. In order for the reaction to proceed to completion, the amino acid has had to be at a pH which is preferably above or more basic than the isoelectric point of the amino acid. For that reason a certain amount of an alkali metal hydroxide, carbonate or bicarbonate has usually been added to the reaction mixture.

Most water soluble salts used in making amino acid chelates have been either sulfates or chlorides. Using the sulfate ion as exemplary, the reaction has generally proceeded as follows:

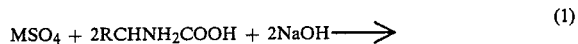

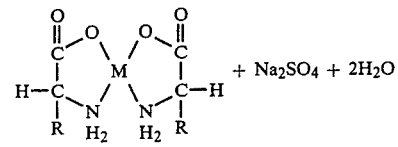

where M is a bivalent metal cation and R is a radical of a naturally occurring amino acid.

It is apparent from the above formula that the sulfate anion is present in the reaction mixture in the form of sodium sulfate. U.S. Pat. No. 2,877,253 teaches a product formed by the reaction of one mole of glycine with one mole of ferrous sulfate. That patent indicates that the sulfate anion becomes tied up in the reaction which allegedly forms a ferrous sulfate-glycine complex.

Hence, whether or not the sulfate actually participates in the reaction or is present as the salt of an alkali metal it nevertheless is present in the reaction mixture. Such products are difficult, if not impossible, to purify. While sodium sulfate per se is water soluble the reaction between a metal sulfate and an amino acid is never carried to 100% completion and the sulfate ion is always present. The same holds true for the presence of chloride ion when utilizing a metal chloride salt for amino chelate preparation.

It would often be desirable to be able to utilize a pure form of amino acid chelates when administering them to biological systems to increase the bioavailability of the metal. For example, the presence of the chloride or sulfate anions may present situations where the administration of the chelate is actually detrimental for the systems requiring divalent metal ions. In non-biological systems it may also be desirable to have a metal present which is not in ionic form and wherein no metal salt anions are present.

Such systems include catalysis, and activation of enzymes. Another area of use not heretofor available is the supplementation of metal ions to plant and soils, soils in particular, where an anion is not also added as part of the supplement. Many soils are deficient in metals such as calcium, magnesium, iron, manganese, copper and zinc but, at the same time, have an excess of chloride and sulfate anions. This is particularly true in areas of salinity where chlorides are present in excess and in areas where acid rain returns excess quantities of sulfate ions to the soil in the form of sulfuric acid. However, the accepted treatment of metal deficient soils is to add materials such as gypsum or kieserite (calcium sulfate) epsom salts (magnesium sulfate), iron sulfate and the like to these soils. This only magnifies the problems when there is an excess of chloride or sulfate anions already in the soil.

Also there are certain industrial systems wherein chelates have been used wherein the presence of an anion is detrimental. Chelates are sometimes utilized to clean ion exchange resins contained in stainless steel tubes. The presence of a chloride or sulfate ion in such systems could have a corrosive action on the interior walls of the stainless steel tube depending upon the pH of the cleaning solution.

Similarly, chelates are utilized as cleaning agents for steam boilers. Again the presence of chloride and/or sulfate ions in a cleaning solution can have a corrosive effect on the boiler surfaces.

OBJECTS AND SUMMARY OF THE INVENTION

It is an object of the present invention to provide pure amino acid chelates free of anion contamination.

It is also an object of the present invention to provide a method of preparing anion free amino acid chelates.

These and other objects may be provided by means of synthetic methods wherein an amino acid ligand is brought into contact with a divalent metal ion in an anion free environment in such a manner that the positive charges on the divalent metal ion are neutralized by the electron rich amino acid ligands with the formation of an amino acid chelate.

One such method for preparing pure amino acids chelates, which have heretofor been unobtainable, is to utilize an electrolytic cell divided into anode and cathode compartments by a selective cation permeable-anion impermeable membrane.

The metal cation is formed in the anode compartment by one of two methods as follows:

$$M \xrightarrow{-e} M^{++} + 2e^- \tag{2}$$

$$MCl \xrightarrow{-e} M^{++} + Cl_2 \uparrow + 2e^- \tag{3}$$

Where M stands for a pure divalent metal.

In the first method the anode is made up of substantially pure M metal which dissolves to form the metal cation. The reaction of the metal cation with the amino acid ligand then takes place in the anode compartment as follows:

$$M^{++} + 2RCHNH_2COOH \longrightarrow \tag{4}$$

[chelate structure] $+ 2H^+$

The hydrogen ions thus formed selectively cross the cation permeable membrane into the cathode compartment where hydrogen gas is formed at the cathode according to the equation:

$$2H^+ + 2e^- \rightarrow H_2 \uparrow \tag{5}$$

The hydrogen gas is then removed from the cathode compartment.

In the second method a metal chloride salt is added to the anode compartment where the metal cation is formed according to equation (3) and the metal cation crosses the cation permeable membrane into the cathode compartment containing an aqueous solution of amino acid ligand where hydrogen is formed at the cathode and the amino acid chelate is formed as follows:

$$M^{++} + 2RCHNH_2COOH + 2e^- \longrightarrow \tag{6}$$

[chelate structure] $+ H_2 \uparrow$

Obviously each reaction in both anode and cathode compartments takes place in aqeuous solutions. It may be necessary in order to induce the proper flow of electrical current through such compartments to add minor amounts of an acid or salt to get the reaction started.

In utilizing either of the above methods the pure amino acid chelate is formed in soluble form and remains in solution. It may be recovered from the solution as a pure water soluble powder by means of evaporation, spray drying or by precipitation by adding a base such as ammonium hydroxide to raise the pH and reduce the solubility of the amino acid chelate.

DETAILED DESCRIPTION OF THE INVENTION

The amino acids of the present invention will ordinarily contain between two to four ligands for each divalent metal ion regardless of the oxidation state or valence of the ion. The following structural formulae, in addition to that shown in equations (1), (4) and (6), are representative of the amino acid chelates which may be prepared in pure form:

[structure] (7)

[structure] (8)

[structure] (9)

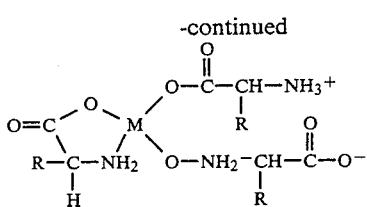

$$\begin{matrix} & & & O \\ & & & \| \\ & & O-C-CH-NH_3^+ \\ O=C & O & M & | \\ & \diagdown & \diagup & R & O \\ & \diagup & \diagdown & & \| \\ R-C-NH_2 & O-NH_2-CH-C-O^- \\ | & & | \\ H & & R \end{matrix} \quad (10)$$

It will be noted in each of these formula that the metal atom is completely neutralized and is carrying no net electical charge. Again, it is to be stressed that these fomulae are representative and that other structures formed by the combination of a divalent metal ion with from two to four amino acid ligands are also within the scope of the present invention as long as a chelate is formed in the absence of an anion.

Even though the prior art depicts the formation of amino acid chelates as if they were pure, the methods of synthesis disclosed in such art is antithetical to the obtaining of the same. In order to form the amino acid chelates in accordance with the processes of the prior art, the proper amounts of constituents must be present under controlled conditions. Since coordination complexes, by definition, are molecular stuctures in which a heterocyclic ring can be formed by the unshared electrons of neighboring atoms, it is important that the acid proton of the amino acid is removed. As a practical matter and as a result of reaction kinetics and conditions, unreacted amino acids, as well as metal salts are found as contaminants in the amino acid chelates produced by the processes of the prior art.

Potentially more harmful than the amino acid contaminants, however, are the residual inorganic anions that are formed in the processes of the prior art and which are present in significant amounts in the amino acid chelates produced by such processes. The anions, generally sulfate and chloride, are present together with lesser amounts of unreacted metal cations in the product mixture, and the anions are virtually impossible to remove from the desired product, i.e., from the amino acid chelate.

In accordance with the present invention pure amino acid chelates are provided which are free of anion contamination. A process for producing such pure amino acid chelates is also provided. The process comprises bringing an amino acid ligand into reactive contact with a divalent metal ion in an environment which is completely anion free but otherwise conducive to the necessary inter action between the amino acid ligand and the metal ion, with the formation of an amino acid chelate in pure form or, at least, which can readily be recovered from the reactive environment in pure form.

One such method for producing the metal cation and the amino acid ligand in a reactive environment which is completely free of contaminating anions utilizes an electrolytic cell which is divided into anode and cathode compartments by a selective cation permeable and anion impermeable membrane. Such membranes are available commercially under the tradename Nafion.

The metal cation is formed in the aqueous electrolyte contained in the anode compartment. This can be achieved by providing a sacrificial anode in the anode compartment which is made of substantially the pure form of the same metal as the desired metal cations. Through the electrolytic action; the metal anode dissolves into the electrolyte in the anode compartment in accordance with equation (2) as given hereinbefore so as to provide the desired metal cations. A second method of providing the desired metal cations is to use an inert anode, with the addition of a metal chloride salt to the anode compartment. In the latter method, the desired metal cations are formed by the electrolytic action on the metal salt in accordance with equation (3) as given hereinbefore, with metal cations forming in the electrolyte within the anode compartment and with gaseous chlorine being released from the electrolyte at the anode.

In the method in which the sacrificial anode is used to provide the metal cations, the amino acid ligand is added to the anode compartment to react with the metal cation in accordance with equation (2) as given hereinabove. The reaction between the ligand and the metal cation produces hydrogen ions which in essence replace the metal cations in the electrolyte in the anode compartment. The hydrogen ions being considerably smaller than the metal cations, pass preferentially through the selective membrane. The hydrogen ions migrate to the cathode in the cathode compartment, and gaseous hydrogen is released in accordance with equation (5) as given hereinabove when the amino acid ligand is completely reacted in the anode compartment, hydrogen ions will no longer be produced, and the generation of hydrogen gas will cease in the cathode compartment. The termination of hydrogen being produced in the cathode compartment is indicative that the conversion of amino acid ligand to metal chelate in the anode compartment has been completed. Pure amino acid chelates free of anion contamination can readily be recovered from the electrolyte of the anode compartment. For example, the electrolyte can be removed from the anode compartment, and the amino acid chelate can be recovered by spray drying or evaporation of the solution, or the amino acid chelate can precipitate from the solution.

In the method in which a metal chloride salt is added to the anode compartment, the membrane separating the anode compartment and the cathode compartment is selected to be of the type which will allow transfer of the metal cation from the anode compartment to the cathode compartment. The metal ions are produced in the anode compartment by the electrolytic decomposition of the metal chloride salt in accordance with equation (3) as given hereinbefore. The metal cations cross the membrane into the cathode compartment which contains an aqueous solution of amino acid ligand. The metal cation reacts with the amino acid ligand to form the amino acid chelate, with gaseous hydrogen being generated at the cathode, all in accordance with equation (6) as given hereinbefore. When the amino acid ligand is depleted in the cathode compartment, hydrogen gas will cease to be generated at the cathode. The termination of hydrogen gas generation can be used to indicate the completion of the reaction. Pure amino acid chelates free of anion contamination can readily be recovered from the electrolyte of the cathode compartment. For example, the electrolyte can be removed from the anode compartment, and the amino acid chelate can be recovered by spray drying or evaporation of the solution, or the amino acid chelate can be precipitated from the solution.

In either of the above methods the amino acid ligand is brought into reactive contact with a divalent metal ion in an aqueous environment which is essentially completely free of inorganic anions. It is to be noted that anytime water is being employed, and especially in an electrolytic process, there will be dissociation of the water into the water forming ions, i.e., hydroxyl ion and hydrogen ion. Thus, the hydroxyl ion will be present. In addition, it has been found that weak organic acids can be used in the aqueous environment to provide at least initial conductance of electrical current by the aqueous solution. The organic anions resulting from the use of the weak organic acids have been found to be readily removable from the metal chelates which are formed. This is in direct contrast to the extreme difficulty experienced in attempting to remove inorganic anion based contaminants from the metal chelates. Thus, for purposes of the present disclosure, whenever the term environment "free of anions" or an equivalent is used in the specification and claims, it is intended to mean free of all anions other than the hydroxyl ion and organic anions. To emphasize, the term "free of anions" as used throughout this specification and accompanying claims is meant to mean essentially exclusive of all anions with the exception of the hydroxyl ion and organic anions resulting from weak organic acids which may be added to the reaction system.

The metal ions which are useful in accordance with the present invention are selected from the group consisting of iron, zinc, manganese, magnesium, copper and calcium. It is anticipated that generally it will be desirable to produce pure metal chelates in which the metal is the same throughout the product. However, there may be instances when a mixture of pure metal chelates may be desired in which the chelates have amino acid ligands combined with two or more differing metals. Such mixtures can readily be produced in accordance with the present invention by utilizing a mixture of metal ions in the reaction with the amino acid ligands.

The amino acid ligands can be any of those selected from the group consisting of naturally occuring amino acids, protein hydrolysates, polypeptides and combinations thereof. It may be that amino acid ligands of essentially one type, such as glycine or other amino acid, may be used. As exemplified in the following examples, the amino acid ligands are provided by the amino acid glycine to the exclusion of other amino acids, protein hydrolysates and polypeptides. However, it is recognized that the amino acid ligands will generally be a mixture of various amino acids, protein hydrolysates and polypeptides which is obtained from hydrolysis of protein material.

In order to more clearly define the invention the following examples of methods of preparing anion free chelates are given. These examples are considered as illustrative only and are not limiting as to the scope of the invention.

EXAMPLE I

An open electrolytic cell was constructed consisting of an anode compartment and a cathode compartment divided by a cation permselective membrane marketed under the tradename Nafion. The anode consisted of pure copper metal and the cathode was made up of. The volume of the anode compartment was approximately 400 cc and the volume of the cathode compartment was about 650 cc. A transformer and rectifier system were utilized to apply a direct current voltage across the cell.

The anolyte solution consisted of an aqeuous glycine having a glycine concentration of about 20% and was circulated continuously throughout the cell compartment and past the anode. The catholyte solution was a 1% citric acid solution. The initial temperature of the anolyte and catholyte solutions was about 40 degrees C. The applied voltage to the transformer was 75 V A.C. The initial voltage across the cell was 5 V D.C. at an amperage of 27 amps.

The temperature within each compartment rose quite rapidly and leveled off at about 90 degrees C. in the anode compartment and 94 degrees C. in the cathode compartment. The amperage slowly increased to about 34 amps and then remained constant and the voltage across the cell decreased slowly during the entire hour of operation from 5 V. D.C. to 2.2 V.D.C.

Upon cooling to room temperature a blue precipitate was formed and separated from the anolyte solution. Upon assay, the blue precipitate was shown to be a copper glycine chelate containing 6% copper and having a ligand to copper ration of 2:1. The resulting chelate precipitate was free of any anions.

The current flow between the anode and cathode compartments was made possible by the migration of hydrogen ions through the cation permselective membrane. Also, upon cooling it was found that certain of the copper ions had also migrated through the membrane and were loosely plated on the cathode.

EXAMPLE II

The same cell utilized in Example I is again used. However, in this example the anode and cathode consists of appropriate inert electrodes.

The anolyte solution is a substantially saturated zinc chloride solution. The catholyte solution is an aqueous glycine solution having a glycine concentration of about 20%.

The cell is placed in a closed hood and current is applied across the cell. The chloride ion migrates to the anode where chlorine gas is formed and escapes into the ventilated hood. The zinc ion migrates through the cation perselective membrane into the cathode compartment. Once in the cathode compartment the zinc ion reacts with the glycine with the concurrent release of hydrogen at the cathode to form a pure chloride free zinc glycine chelate.

I claim:

1. An amino acid chelate consisting of a metal ion selected from the group consisting of iron, zinc, manganese, magnesium, cooper, calcium and mixtures thereof chelated to one or more ligands selected from the group consisting of alpha amino acids, protein hydrolysates, polypeptides and dipeptides and combinations theron wherein said chelate is essentially free of anion radicals other than hydroxyl and anions of weak organic acids.

2. An amino acid chelate in accordance with claim 1, wherein the metal ion is chelated with from 1 to 4 ligands.

3. A method of preparing an amino acid chelate essentially free of anion radicals other than hydroxyl and anions of weak organic acids which comprises the steps consisting of:
   (a) providing an electrolytic cell having anode and cathode compartments divided by a cation permselective membrane wherein the anode is made up of a substantially pure form of the metal or metals to be used in preparing the chelate,
   (b) placing an aqueous solution of an amino acid ligand in the anode compartment and electrolyte aqueous solution in the cathode compartment,
   (c) applying a direct current across said cell causing the anode metal to dissolve into said aqeuous amino acid ligand solution and react with said amino acid ligand to form an amino acid chelate and wherein hydrogen ions are caused to migrate from said anode solution across said membrane into said cathode compartment where hydrogen gas is released at said cathode, and (d) recovering said amino acid chelate in substantially pure form from said anode solution.

4. A method of preparing an amino acid chelate essentially free on anion radicals other than hydroxyl and anions of weak organic acids which comprises the steps consisting of:

(a) providing an electrollytic cell having anode and cathode compartment divided by a cation permselective membrane, (b) introducing an aqueous metal chloride salt solution into said anode compartment and an aqueous amino acid ligand solution into said cathode compartment, (c) applying a direct current across said cell causing the chloide ion to migrate to said anode and be released as chlorine gas therefrom, and causing the metal ion to migrate across said cation permselective membrane into said cathode compartment wherein said metal ion reacts with said amino acid ligand to form an amino acid chelate, and (d) recovering said amino acid chelate in substantially pure form from said cathode compartment.

5. A method according to claim 3 wherein said anode is made up of a metal or metals selected from the group consisting of iron, zinc, manganese, magnesium, copper and calcium.

6. A method according to claim 5 wherein said amino acid ligand utilized to form an aqueous solution and placed in said anode compartment is selected from the group consisting of naturally occuring amino acids, protein hydrolysates, polypeptides, dipeptides and mixtures thereof.

7. A method according to claim 4 wherein said metal chloride salt utilized to form an aqueous solution and placed in said anode compartment is selected from the group consisting of iron chloride, zinc chloride, manganese chloride, magnesium chloride, copper chloride and calcium chloride and mixtures thereof.

8. A method according to claim 7 wherein said amino acid ligand utilized to form an aqueous solution and placed in said cathode compartment is selected from the group consisting of naturally occuring amino acids, protein hydrolysates, polypeptides, dipeptides and mixtures thereof.

* * * * *